(12) United States Patent
Wood (10) Patent No.: US 11,083,481 B2
(45) Date of Patent: Aug. 10, 2021

(54) TISSUE RESECTING INSTRUMENT INCLUDING AN OUTFLOW CONTROL SEAL

(71) Applicant: Covidien LP, Mansfield, MA (US)

(72) Inventor: Timothy J. Wood, Wilmington, MA (US)

(73) Assignee: Covidien LP, Mansfield, MA (US)

( * ) Notice: Subject to any disclaimer, the term of this patent is extended or adjusted under 35 U.S.C. 154(b) by 371 days.

(21) Appl. No.: 16/282,417

(22) Filed: Feb. 22, 2019

(65) Prior Publication Data

US 2020/0268946 A1 Aug. 27, 2020

(51) Int. Cl.
  *A61B 17/32* (2006.01)
  *A61M 1/00* (2006.01)
  *A61B 17/42* (2006.01)

(52) U.S. Cl.
  CPC ..... *A61B 17/32002* (2013.01); *A61M 1/0035* (2014.02); *A61B 2017/32004* (2013.01); *A61B 2017/320032* (2013.01); *A61B 2017/4216* (2013.01); *A61B 2217/005* (2013.01)

(58) Field of Classification Search
  CPC ........... A61M 1/0035; A61B 17/32002; A61B 2017/320032; A61B 2017/32004; A61B 2017/4216; A61B 2217/005
  See application file for complete search history.

(56) References Cited

U.S. PATENT DOCUMENTS

| | | | |
|---|---|---|---|
| 1,585,934 A | 5/1926 | Muir | |
| 1,666,332 A | 4/1928 | Hirsch | |
| 1,831,786 A | 11/1931 | Duncan | |
| 2,708,437 A | 5/1955 | Hutchins | |
| 3,297,022 A | 1/1967 | Wallace | |
| 3,686,706 A | 8/1972 | Finley | |

(Continued)

FOREIGN PATENT DOCUMENTS

| | | | |
|---|---|---|---|
| DE | 102010050352 A1 | 5/2012 | |
| EP | 2397084 A2 | 12/2011 | |

(Continued)

OTHER PUBLICATIONS

Extended European Search Report issued in corresponding European Application No. 20158825.8 dated Jun. 12, 2020, 10 pages.

*Primary Examiner* — Sarah A Simpson
(74) *Attorney, Agent, or Firm* — Carter, DeLuca & Farrell LLP (57) ABSTRACT

A tissue resecting instrument includes an end effector assembly having a proximal hub housing, outer and inner shafts extending therefrom, and an inner core drive assembly to rotate and reciprocate the inner shaft relative to the outer shaft. The inner core drive assembly includes a proximal receiver that receives a rotational input and rotates in response and includes a seal member disposed thereon. The rotation of the proximal receiver effects rotation of a connector and reciprocation of the connector between a proximal position and a distal position. The connector is operably coupled to the inner shaft such that the rotation and reciprocation of the connector effects the rotation and reciprocation of the inner shaft. In the proximal position, the connector and the seal member establish a seal that blocks outflow. In the distal position, the connector is displaced from the seal member to permit outflow.

20 Claims, 7 Drawing Sheets

(56) References Cited

U.S. PATENT DOCUMENTS

| | | |
|---|---|---|
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brady |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grassi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |

(56) References Cited

U.S. PATENT DOCUMENTS

| | | |
|---|---|---|
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,171,316 B1 | 1/2001 | Kovac et al. |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,293,957 B1 | 9/2001 | Peters et al. |
| 6,315,714 B1 | 11/2001 | Akiba |
| 6,358,200 B1 | 3/2002 | Grassi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,663,641 B1 | 12/2003 | Kovac et al. |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,062,214 B2 | 11/2011 | Shener et al. |
| 8,419,626 B2 | 4/2013 | Shener-Irmakoglu et al. |
| 8,574,253 B2 | 11/2013 | Gruber et al. |
| 8,663,264 B2 | 3/2014 | Cesarini et al. |
| 8,678,999 B2 | 3/2014 | Isaacson |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,125,550 B2 | 9/2015 | Shener-Irmakoglu et al. |
| 9,155,454 B2 | 10/2015 | Sahney et al. |
| 2001/0039963 A1 | 11/2001 | Spear et al. |
| 2001/0047183 A1 | 11/2001 | Privitera et al. |
| 2002/0058859 A1 | 5/2002 | Brommersma |
| 2002/0165427 A1 | 11/2002 | Yachia et al. |
| 2003/0050603 A1 | 3/2003 | Todd |
| 2003/0050638 A1 | 3/2003 | Yachia et al. |
| 2003/0078609 A1 | 4/2003 | Finlay et al. |
| 2003/0114875 A1 | 6/2003 | Sjostrom |
| 2004/0010258 A1 | 1/2004 | Carusillo et al. |
| 2004/0092980 A1* | 5/2004 | Cesarini ........... A61B 17/32002 606/159 |
| 2004/0204671 A1 | 10/2004 | Stubbs et al. |
| 2004/0220602 A1 | 11/2004 | Deng et al. |
| 2005/0043690 A1 | 2/2005 | Todd |
| 2005/0085692 A1 | 4/2005 | Kiehn et al. |
| 2005/0240206 A1 | 10/2005 | Sjostrom |
| 2006/0036132 A1 | 2/2006 | Renner et al. |
| 2006/0047185 A1 | 3/2006 | Shener et al. |
| 2006/0161191 A1 | 7/2006 | Bucina |
| 2006/0241586 A1 | 10/2006 | Wilk |
| 2008/0015621 A1 | 1/2008 | Emanuel |
| 2008/0058588 A1 | 3/2008 | Emanuel |
| 2008/0058672 A1* | 3/2008 | Shabaz .............. A61B 10/0275 600/566 |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0125287 A1 | 5/2010 | Cole et al. |
| 2010/0152647 A1 | 6/2010 | Shener et al. |
| 2011/0166419 A1 | 7/2011 | Reif et al. |
| 2012/0078038 A1 | 3/2012 | Sahney et al. |
| 2012/0209289 A1 | 8/2012 | Duque et al. |
| 2012/0253227 A1 | 10/2012 | Shener-Irmakoglu et al. |
| 2013/0131452 A1 | 5/2013 | Kuroda et al. |
| 2013/0310864 A1* | 11/2013 | Jezierski .......... A61B 17/32002 606/170 |
| 2014/0031834 A1 | 1/2014 | Germain et al. |
| 2017/0020545 A1 | 1/2017 | Loreth |
| 2018/0028212 A1* | 2/2018 | Akilian .......... A61B 17/320783 |
| 2018/0318133 A1 | 11/2018 | Clauson et al. |

FOREIGN PATENT DOCUMENTS

| | | |
|---|---|---|
| EP | 1753350 B1 | 8/2014 |
| EP | 3275381 A1 | 1/2018 |
| WO | 2015023965 A1 | 2/2015 |

\* cited by examiner

TISSUE RESECTING INSTRUMENT INCLUDING AN OUTFLOW CONTROL SEAL

BACKGROUND

1. Technical Field

The present disclosure relates generally to the field of tissue resection. In particular, the present disclosure relates to a tissue resecting instrument including an outflow control seal.

2. Background of Related Art

Tissue resection may be performed endoscopically within an organ, such as a uterus, by inserting an endoscope (or hysteroscope) into the uterus and passing a tissue resection instrument through the endoscope (or hysteroscope) and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space.

SUMMARY

As used herein, the term "distal" refers to the portion that is described which is further from a user, while the term "proximal" refers to the portion that is described which is closer to a user. Further, to the extent consistent, any or all of the aspects described herein may be used in conjunction with any or all of the other aspects described herein.

Provided in accordance with aspects of the present disclosure is an end effector assembly of a tissue resecting instrument. The end effector assembly includes a proximal hub housing, an outer shaft extending from the proximal hub housing, an inner shaft disposed within the outer shaft and configured to rotate and reciprocate relative to the outer shaft for cutting tissue, and an inner core drive assembly disposed at least partially within the proximal hub housing. The inner core drive assembly is operably coupled to the inner shaft and configured such that a rotational input provided to the inner core drive assembly effects the rotation and reciprocation of the inner shaft relative to the outer shaft. The inner core drive assembly includes a proximal receiver configured to receive the rotational input and to rotate relative to the proximal hub housing in response thereto. The proximal receiver includes a seal member disposed thereon. The inner core drive assembly further includes a connector operably coupled to the proximal receiver such that the rotation of the proximal receiver effects rotation of the connector relative to the proximal hub housing and reciprocation of the connector relative to the proximal receiver and the proximal hub housing between a proximal position and a distal position. The connector is operably coupled to the inner shaft such that the rotation and reciprocation of the connector effects the rotation and reciprocation of the inner shaft. The connector defines a cavity disposed in fluid communication with an interior of the inner shaft. In the proximal position, the connector abuts the seal member to establish a seal that blocks outflow from the cavity. In the distal position, the connector is displaced from the seal member to permit outflow from the cavity.

In an aspect of the present disclosure, the inner core drive assembly further includes a threaded coupler operably coupled to the connector and a follower operably engaged with the threaded coupler. The rotation of the connector in response to the rotation of the proximal receiver rotates the threaded coupled relative to the follower, thereby reciprocating the threaded coupler and the connector relative to the proximal receiver.

In another aspect of the present disclosure, the connector is rotationally fixed relative to the proximal receiver via at least partial receipt of a distal spine of the proximal receiver within the cavity of the connector.

In another aspect of the present disclosure, the distal spine is slidable relative to the cavity of the connector to permit the reciprocation of the connector relative to the proximal receiver.

In still another aspect of the present disclosure, the seal member is disposed about the distal spine.

In yet another aspect of the present disclosure, the reciprocation of the connector effects similar reciprocation of the inner shaft.

In still yet another aspect of the present disclosure, gearing is operably coupled between the connector and the inner shaft such that the rotation of the inner shaft is amplified or attenuated relative to the rotation of the connector.

In another aspect of the present disclosure, the outer shaft defines a window and the inner shaft is configured to rotate and reciprocate relative to the window to cut tissue extending through the window.

In yet another aspect of the present disclosure, the proximal position of the connector corresponds to a proximal position of the inner shaft relative to the outer shaft.

A tissue resecting instrument provided in accordance with aspects of the present disclosure includes a handpiece assembly including a drive rotor and an outflow conduit, and an end effector assembly configured to releasably engage the handpiece assembly. The end effector assembly includes an outer shaft, an inner shaft disposed within the outer shaft and configured to rotate and reciprocate relative to the outer shaft for cutting tissue, and an inner core drive assembly. The inner core drive assembly includes a proximal receiver configured to receive a rotational input from the drive rotor and to rotate in response thereto. The proximal receiver includes a seal member disposed thereon. The inner core drive assembly further includes a connector operably coupled to the proximal receiver such that the rotation of the proximal receiver effects rotation of the connector and reciprocation of the connector between a proximal position and a distal position. The connector is operably coupled to the inner shaft such that the rotation and reciprocation of the connector effects the rotation and reciprocation of the inner shaft. The connector defines a cavity disposed in fluid communication with an interior of the inner shaft. In the proximal position, the connector abuts the seal member to establish a seal that blocks outflow from the cavity into the outflow conduit. In the distal position, the connector is displaced from the seal member to permit outflow from the cavity into the outflow conduit.

In an aspect of the present disclosure, the handpiece assembly further includes a motor configured to drive rotation of the drive rotor.

In another aspect of the present disclosure, the inner core drive assembly further includes a threaded coupler operably coupled to the connector and a follower operably engaged with the threaded coupler. The rotation of the connector in response to the rotation of the proximal receiver rotates the threaded coupled relative to the follower, thereby reciprocating the threaded coupler and the connector relative to the proximal receiver.

In still another aspect of the present disclosure, the connector is rotationally fixed relative to the proximal receiver via at least partial receipt of a distal spine of the proximal receiver within the cavity of the connector. In such aspects, the distal spine may be slidable relative to the cavity of the connector to permit the reciprocation of the connector relative to the proximal receiver. Additionally or alternatively, the seal member is disposed about the distal spine.

In yet another aspect of the present disclosure, wherein the reciprocation of the connector effects similar reciprocation of the inner shaft.

In still yet another aspect of the present disclosure, gearing is operably coupled between the connector and the inner shaft such that the rotation of the inner shaft is amplified or attenuated relative to the rotation of the connector.

In another aspect of the present disclosure, the outer shaft defines a window and the inner shaft is configured to rotate and reciprocate relative to the window to cut tissue extending through the window.

In an aspect of the present disclosure, the proximal position of the connector corresponds to a proximal position of the inner shaft relative to the outer shaft.

In another aspect of the present disclosure, the drive rotor is configured to provide a further rotational input to the proximal receiver after the rotational input to the proximal receiver to return the connector to the proximal position, thereby establishing the seal that blocks outflow from the cavity into the outflow conduit.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
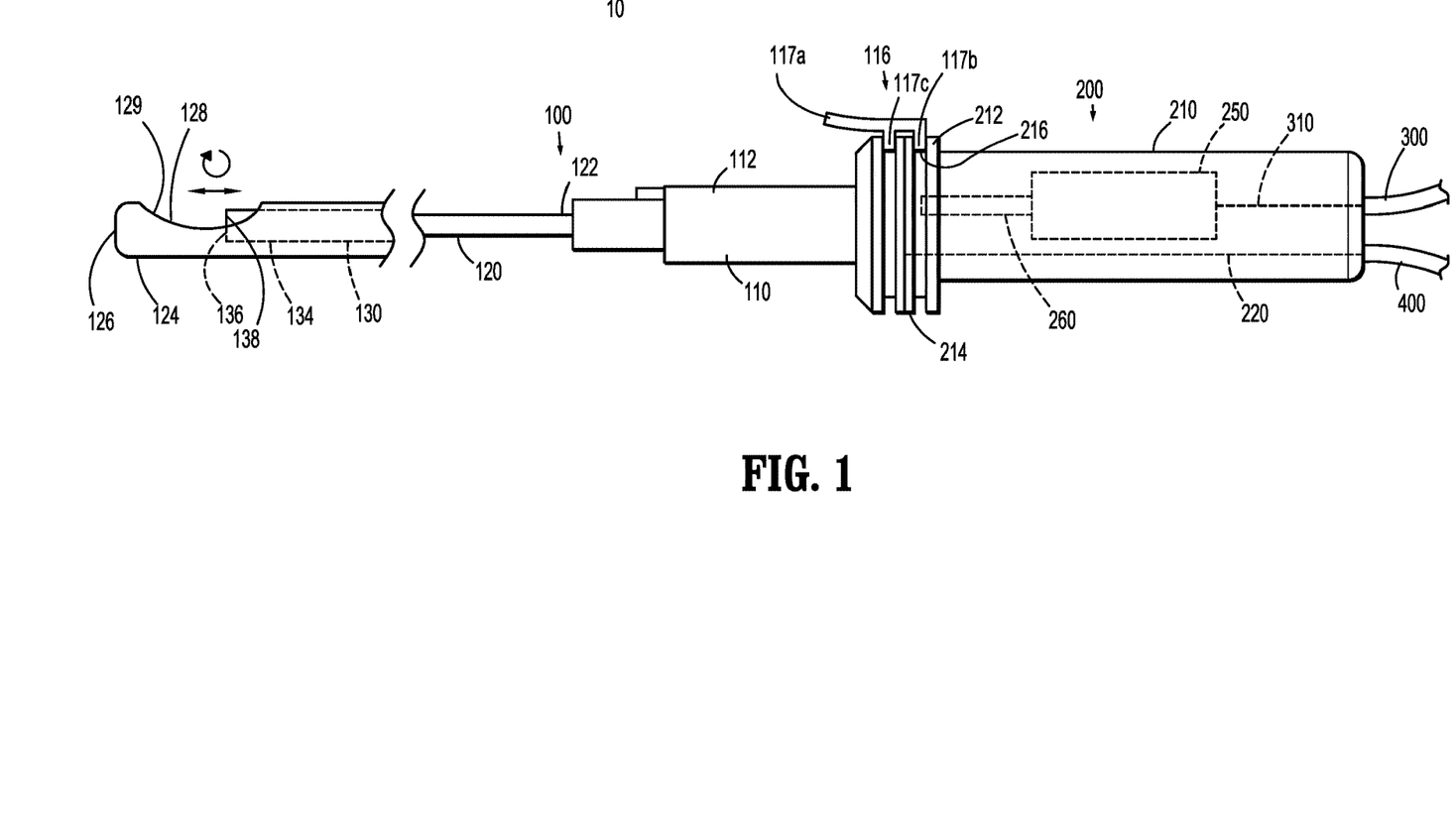
FIG. 1 is a side view of a tissue resecting instrument provided in accordance with aspects of the present disclosure including a handpiece assembly and an end effector assembly, wherein a distal end portion of the end effector assembly is enlarged to better illustrate features thereof.

Referring generally to FIG. 1, a tissue resecting instrument 10 provided in accordance with the present disclosure and configured to resect tissue includes an end effector assembly 100 and a handpiece assembly 200. Tissue resecting instrument 10 is adapted to connect to a control unit (not shown) via a cable 300 to provide power and control functionality to tissue resecting instrument 10, although tissue resecting instrument 10 may alternatively or additionally include controls associated with handpiece assembly 200 and/or a power source, e.g., battery, disposed within handpiece assembly 200. Tissue resecting instrument 10 is further adapted to connect to a fluid management system (not shown) via outflow tubing 400 for applying suction to remove fluid, tissue, and debris from a surgical site via tissue resecting instrument 10, as detailed below. The control unit and fluid management system may be integral with one another, coupled to one another, or separate from one another.

Tissue resecting instrument 10 may be configured as a single-use device that is discarded after use or sent to a manufacturer for reprocessing, a reusable device capable of being cleaned and/or sterilized for repeated use by the end-user, or a partially-single-use, partially-reusable device. With respect to partially-single-use, partially-reusable configurations, handpiece assembly 200 may be configured as a cleanable/sterilizable, reusable component, while end effector assembly 100 is configured as a single-use, disposable/reprocessable component. In any of the above configurations, end effector assembly 100 is configured to releasably engage handpiece assembly 200 to facilitate disposal/reprocessing of any single-use components and cleaning and/or sterilization of any reusable components. Further, enabling releasable engagement of end effector assembly 100 with handpiece assembly 200 allows for interchangable use of different end effector assemblies, e.g., different length, configuration, etc., end effector assemblies, with handpiece assembly 200.

Continuing with reference to FIG. 1, handpiece assembly 200 generally includes a handle housing 210, an outflow conduit 220 defined through (as shown), extending through, disposed on, or otherwise associated with handle housing 210, a motor 250 disposed within handle housing 210, and a drive rotor 260 disposed at least partially within handle housing 210 and operably coupled to motor 250. Handpiece assembly 200 may further include one or more controls (not shown) disposed on or operably associated with handle housing 210 to facilitate activation of tissue resecting instrument 10. Further, outflow tubing 400 is configured to connect to a proximal end portion of outflow conduit 220 to thereby connect outflow conduit 220 to the fluid management system (not shown). The fluid management system includes a vacuum source to establish suction through tissue resecting instrument 10 and outflow tubing 400 to facilitate removal of fluid, tissue, and debris from the surgical site and may also include a collection reservoir, e.g., a collection canister, for collecting the removed fluid, tissue, and debris. As an alternative or in addition to a vacuum source establishing suction through tissue resecting instrument 10 and outflow tubing 400, vacuum may be created therethrough via a pressure differential between the surgical site and the outflow path.

Handle housing 210 defines a pencil-grip configuration, although other configurations are also contemplated, e.g., pistol-grip configurations, and includes a distal hub 212 disposed at an open distal end portion 214 thereof. Distal hub 212 defines an annular recess 216 configured to facilitate releasably engagement of end effector assembly 100 with handpiece assembly 200, as detailed below. Open distal end portion 214 of handle housing 210 provides access to drive rotor 260 and a distal end portion of outflow conduit 220 within handle housing 210 such that, upon engagement of end effector assembly 100 with handpiece assembly 200, as also detailed below, a portion of end effector assembly 100 extends through open distal end portion 214 and into the interior of handle housing 210 to operably couple with drive rotor 260 and a distal end portion of outflow conduit 220.

Cable 300 extends proximally from handle housing 210 and is configured to connect to the control unit (not shown) to provide power and control functionality to tissue resecting instrument 10. Cable 300, more specifically, houses one or more wires 310 that extend into handle housing 210 and connect to the controls thereof and/or motor 250 to power motor 250 and control operation of tissue resecting instrument 10 in accordance with controls associated with handpiece assembly 200, the control unit, and/or other remote control devices, e.g., a footswitch (not shown).

Drive rotor 260 is operably coupled with and extends distally from motor 250 such that, upon activation of motor 250, motor 250 drives rotation of drive rotor 260. At least a portion of drive rotor 260 defines a non-circular cross-sectional configuration, e.g., a square or other polygonal configuration. Drive rotor 260 is configured for at least partial receipt within proximal receiver 146 of end effector assembly 100 (see FIG. 2) in fixed rotational orientation relative thereto upon engagement of end effector assembly 100 with handpiece assembly 200. As such, activation of motor 250 drives rotation of drive rotor 260 to, in turn, drive rotation of inner cutting shaft 130 of end effector assembly 100, as detailed below.

Figure 2:
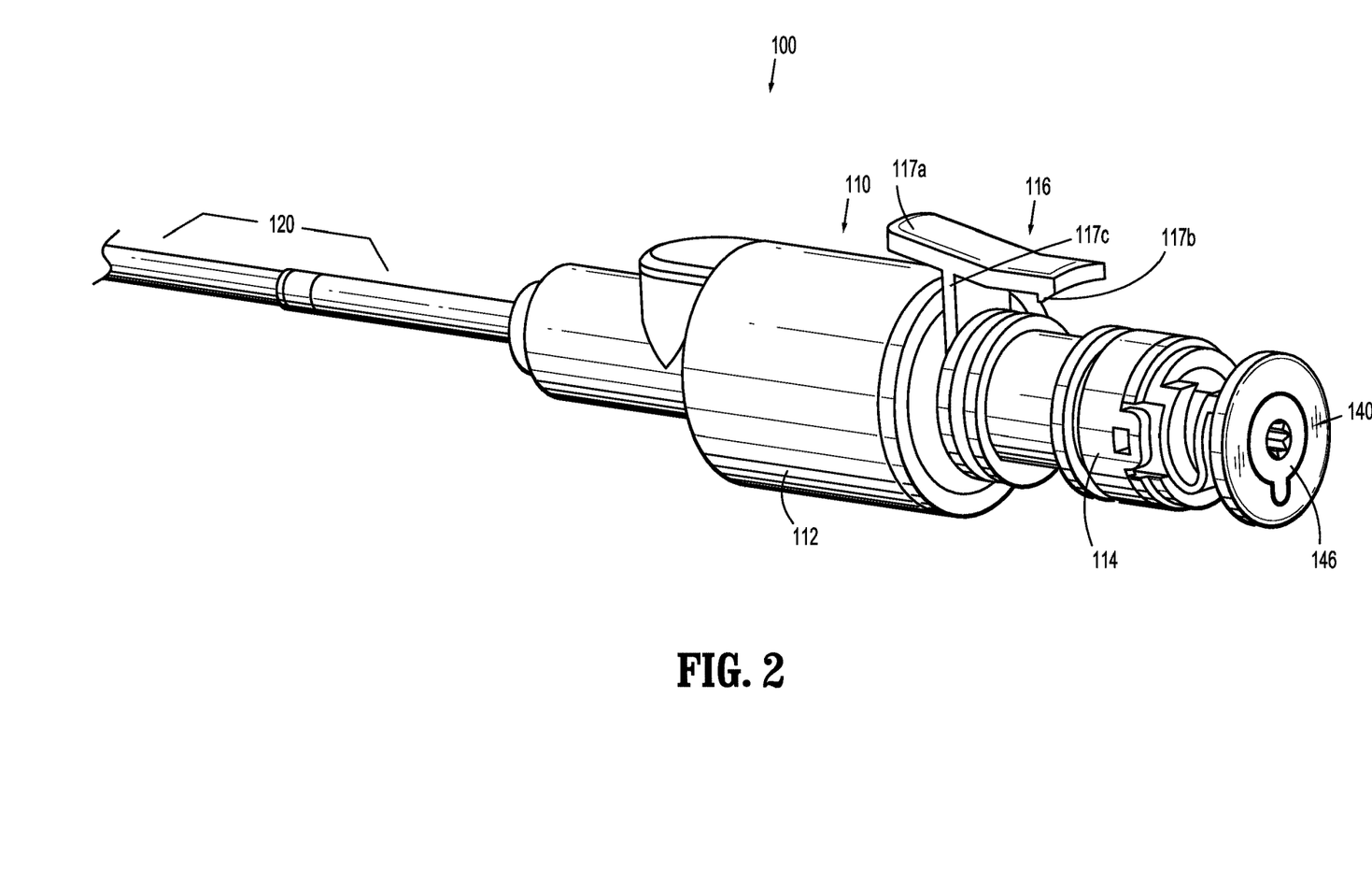
FIG. 2 is a perspective view of the end effector assembly of the tissue resecting instrument of FIG. 1.
Figure 3:
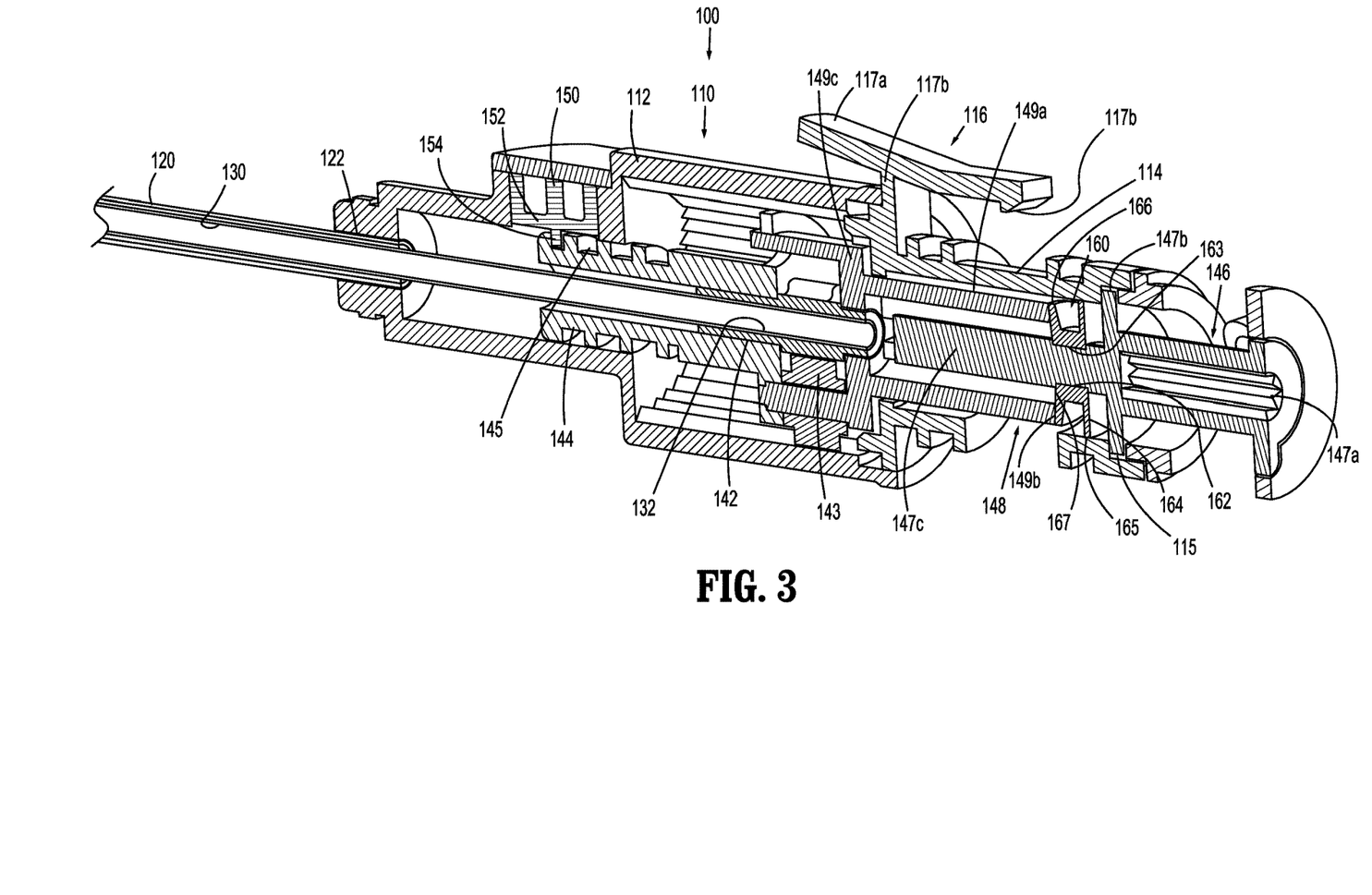
FIG. 3 is a longitudinal, cross-sectional view of the end effector assembly of FIG. 2.

Referring to FIGS. 1-3, end effector assembly 100 includes a proximal hub housing 110, an elongated outer shaft 120 monolithically formed, fixedly engaged, or otherwise connected with and extending distally from proximal hub housing 110, an inner cutting shaft 130 disposed within elongated outer shaft 120, and an inner core drive assembly 140.

Proximal hub housing 110 of end effector assembly 100 includes a distal body portion 112 and a proximal extension portion 114 that may be monolithically formed, engaged, or otherwise connected to one another. With end effector assembly 100 engaged with handpiece assembly 200, proximal extension portion 114 of proximal hub housing 110 extends into handle housing 210 of handpiece assembly 200 while distal body portion 112 substantially abuts and extends distally from handle housing 210 of handpiece assembly 200. An engagement lever 116 extends from proximal hub housing 110. Engagement lever 116 includes a finger tab 117a and an engagement tooth 117b disposed on opposite sides of a living hinge pivot 117c such that urging finger tab 117a towards proximal hub housing 110 urges engagement tooth 117b away from proximal hub housing 110, and vice versa.

Upon insertion of proximal extension portion 114 of proximal hub housing 110 of end effector assembly 100 into handle housing 210 of handpiece assembly 200, engagement tooth 117b is configured to cam over distal hub 212 of handpiece assembly 200 and into engagement within annular recess 216 of distal hub 212 of handpiece assembly 200 to engage end effector assembly 100 and handpiece assembly 20 with one another. Disengagement of end effector assembly 100 from handpiece assembly 200 is effected by depressing finger tab 117a towards proximal hub housing 110 to thereby withdraw engagement tooth 117b from annular recess 216. With engagement tooth 117b disengaged from annular recess 216, end effector assembly 100 may be moved distally relative to handpiece assembly 200 to withdraw proximal extension portion 114 from handle housing 210, thereby disengaging end effector assembly 100 from handpiece assembly 200.

With reference to FIG. 1, elongated outer shaft 120 of end effector assembly 100, as noted above, includes a proximal end portion 122 fixedly engaged with distal body portion 112 of proximal hub housing 110 (see FIG. 3). Elongated outer shaft 120 further includes a distal end portion 124 defining a closed distal end 126 and a window 128 proximally-spaced from closed distal end 126. Window 128 provides access to the interior of elongated outer shaft 120 and may be surrounded by a cutting edge 129 about the outer perimeter of window 128 so as to facilitate cutting of tissue passing through window 128 and into elongated outer shaft 120.

Inner cutting shaft 130 of end effector assembly 100 extends through elongated outer shaft 120 and defines a proximal end portion 132 and a distal end portion 134 defining an open distal end 136. Proximal end portion 132 of inner cutting shaft 130 is operably coupled with inner core drive assembly 140, as detailed below (see FIG. 3). Inner cutting shaft 130 defines an annular cutting edge 138 surrounding open distal end 136 so as to facilitate cutting of tissue passing into inner cutting shaft 130 via open distal end 136. Inner cutting shaft 130 is rotatable and reciprocatable within and relative to elongated outer shaft 120. More specifically, inner cutting shaft 130 is configured to reciprocate and rotate such that annular cutting edge 138 is exposed within window 128 of elongated outer shaft 120 during at least a portion of the reciprocation motion of inner cutting shaft 130 to enable cutting of tissue therewith. As detailed below, suction is provided to facilitate drawing tissue into window 128 of elongated outer shaft 120 and, thus, to facilitate the cutting of tissue with inner cutting shaft 130 and removal of tissue through inner cutting shaft 130. Other suitable configurations of elongated outer shaft 120 and/or inner cutting shaft 130 that cooperate to facilitate tissue cutting are also contemplated.

Referring to FIGS. 2 and 3, inner core drive assembly 140 is partially disposed within proximal hub housing 110 and extends proximally from proximal hub housing 110 to facilitate operable engagement with handpiece assembly 200. Further, inner core drive assembly 140 is coupled to inner cutting shaft 130 within proximal hub housing 110 such that rotational input imparted to inner core drive assembly 140, e.g., via handpiece assembly 200, drives reciprocation and rotation of inner cutting shaft 130 within and relative to elongated outer shaft 120, as detailed below.

Inner core drive assembly 140, more specifically, includes a ferrule 142 fixedly engaged about proximal end portion 132 of inner cutting shaft 130, a threaded coupler 144, a proximal receiver 146, and a connector 148 operably coupling ferrule 142, threaded coupler 144, and proximal receiver 146 with one another, as detailed below. Inner core drive assembly 140 further includes a follower 150 fixed relative to proximal hub housing 110. Follower 150 includes a cap 152 fixedly engaged with proximal hub housing 110 and an arm 154 extending from cap 152 into operable engagement with helical channel 145 of threaded coupler 144.

Figure 4:
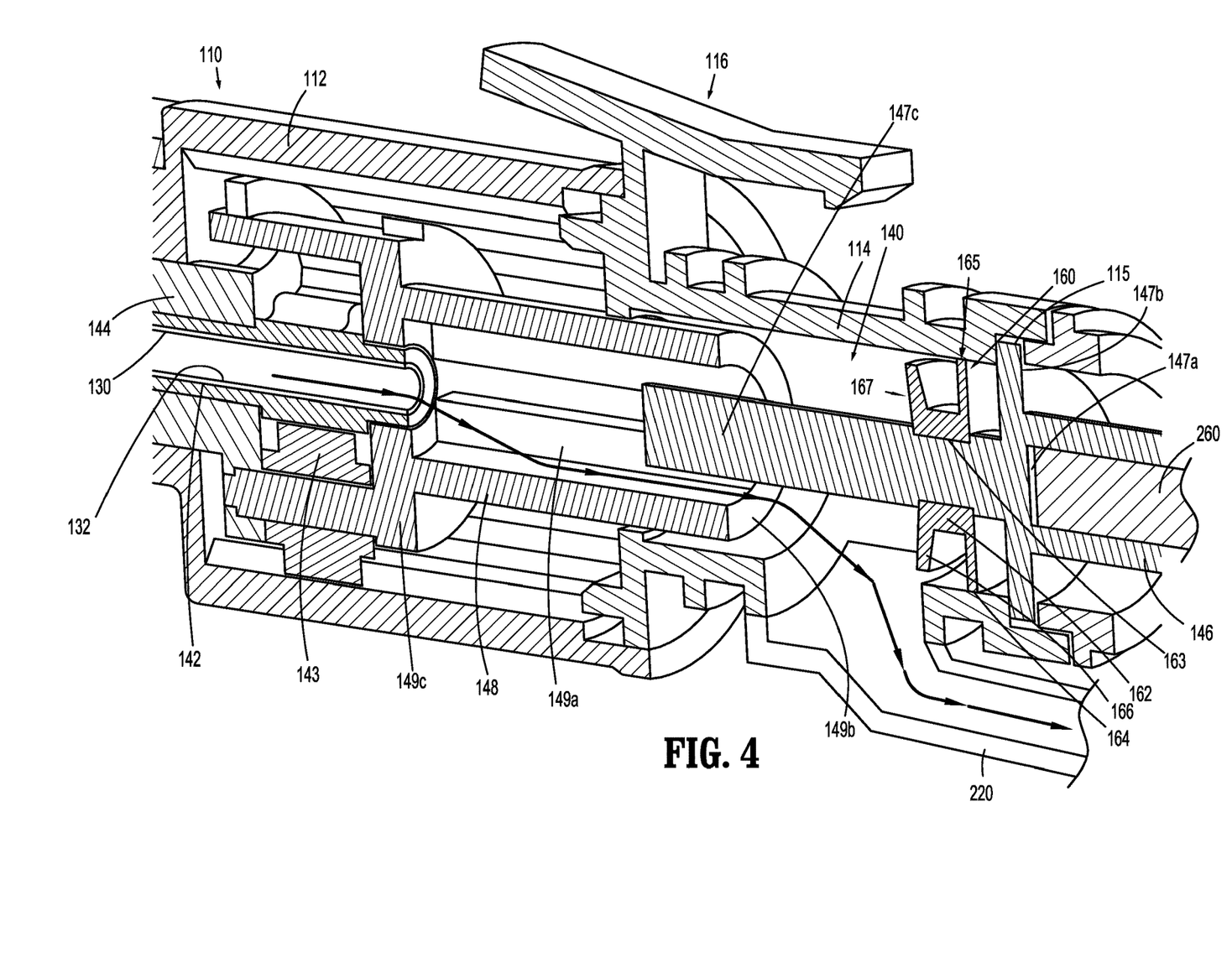
FIG. 4 is a longitudinal, cross-sectional view of a portion of the tissue resecting instrument of FIG. 1 with the end effector assembly operably coupled to a drive rotor of the handpiece assembly and fluidly coupled to an outflow conduit of the handpiece assembly, wherein the remainder of the handpiece assembly is removed.
Figure 5:
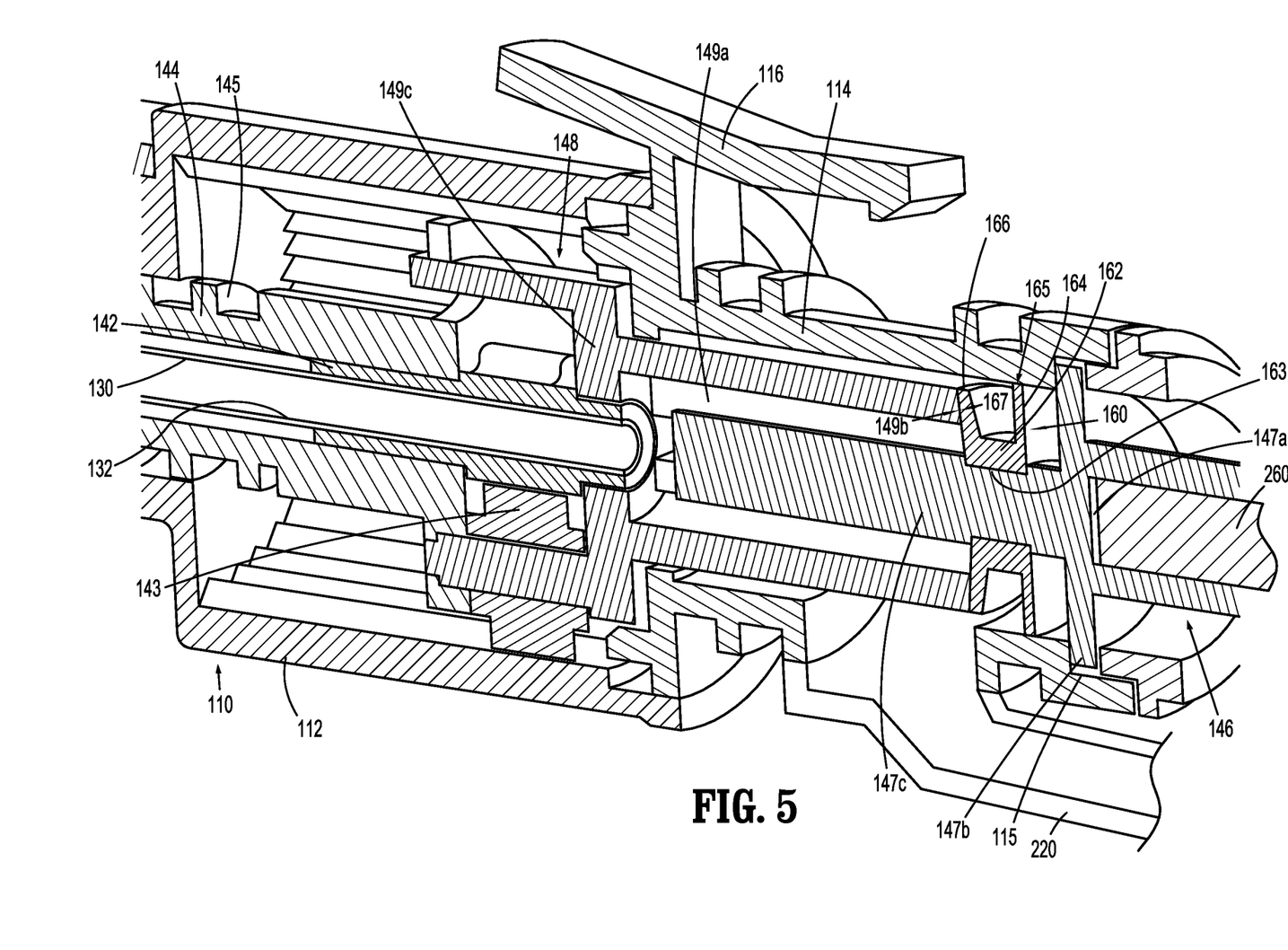
FIG. 5 is a longitudinal, cross-sectional view of the portion of the tissue resecting instrument of FIG. 1 illustrated in FIG. 4, with the end effector assembly operably coupled to the drive rotor of the handpiece assembly and sealed from the outflow conduit of the handpiece assembly, wherein the remainder of the handpiece assembly is removed.

Continuing with reference to FIGS. 2 and 3, proximal receiver 146 of inner core drive assembly 140 includes a proximally-facing cavity 147a at least a portion of which has a non-circular cross-sectional configuration, e.g., an 8-point star or other polygonal configuration, that is configured to at least partially receive drive rotor 260 of handpiece assembly 200 in fixed rotational orientation (see FIGS. 4 and 5). Proximal receiver 146 further includes a central collar 147b received within an interior annular recess 115 defined within proximal extension portion 114 of proximal hub housing 110 to longitudinally fixed and rotatably couple proximal receiver 146 relative to proximal hub housing 110. Proximal receiver 146 additionally includes a distal spine 147c extending distally from central collar 147b and a seal member 160 engaged about distal spine 147c. At least a portion of distal spine 147c defines a non-circular cross-sectional configuration, e.g., a rectangular or other polygonal configuration.

Connector 148 defines a proximally-facing cavity 149a at least a portion of which has a non-circular cross-sectional configuration, e.g., a rectangular or other polygonal configuration, that is configured to receive at least a portion of distal spine 147c of proximal receiver 146 in fixed rotational orientation while permitting relative translation therebetween. Connector 148 additionally includes an annular, proximally-facing surface 149b surrounding proximally-facing cavity 149a. Proximally-facing surface 149b may be a substantially flat, smooth surface to facilitate establishing a fluid-tight seal between proximally-facing surface 149b and seal member 160, as detailed below. Connector 148 further includes a distal body 149c that is fixedly engaged with threaded coupler 144 and operably engaged with ferrule 142 to thereby translationally fix and rotationally couple connector 148 and threaded coupler 144 with inner cutting shaft 130. Distal body 149c of connector 148, more specifically, is operably engaged with ferrule 142 via gearing 143 to amplify or attenuate the rotational input to inner cutting shaft 130 relative to the rotation output from drive rotor 260. Alternatively, distal body 149c of connector 148 may be fixedly engaged about ferrule 142 (or operably coupled via a 1:1 gear ratio or other suitable 1:1 input to output ratio) such that the rotation imparted to inner cutting shaft 130 is equal to the rotational output from drive rotor 260. In either configuration, ferrule 142 and connector 148 are positioned relative to proximal end portion 132 of inner cutting shaft 130 such that proximally-facing cavity 149a of connector 148 is disposed in fluid communication with the interior of inner cutting shaft 130 via the open proximal end of inner cutting shaft 130.

Turning to FIGS. 4 and 5, in use, motor 250 of handpiece assembly 200 (see FIG. 1) is activated to drive rotation of drive rotor 260. Upon activation of motor 250 (FIG. 1), with a head-start or delay relative to activation of motor 250, or independently thereof, suction is established through outflow conduit 220 of handpiece assembly 200 and outflow tubing 400, e.g., via activating the vacuum source of the fluid management system.

Due to the fixed rotational engagement of drive rotor 260 at least partially within proximally-facing cavity 147a of proximal receiver 146 of inner core drive assembly 140, rotation of drive rotor 260 effects similar rotation of proximal receiver 146. Rotation of proximal receiver 146 relative to proximal hub housing 110, in turn, is transmitted to connector 148 via the fixed rotational engagement of distal spine 147c of proximal receiver 146 at least partially within proximally-facing cavity 149a of connector 148. This rotation imparted to connector 148, in turn, is transmitted to threaded coupler 144 via the fixed engagement of distal body 149c of connector 148 therewith.

Further, due to the operable engagement of arm 154 of follower 150 within helical channel 145 of threaded coupler 144, the imparted rotation to threaded coupler 144 reciprocates threaded coupler 144 and, thus, also reciprocates connector 148 relative to proximal hub housing 110 and proximal receiver 146 (whereby distal spine 147c of proximal receiver 146 reciprocates within proximally-facing cavity 149a of connector 148). The reciprocation and rotation of threaded coupler 144 and connector 148 is also transmitted to inner cutting shaft 130 by way of gearing 143 and ferrule 142 such that inner cutting shaft 130 is rotated and reciprocated within and relative to elongated outer shaft 120. While gearing 143 may vary the rotation of inner cutting shaft 130 relative to threaded coupler 144 and connector 148, inner cutting shaft 130 is reciprocated similarly as threaded coupler 144 and connector 148.

With additional reference to FIG. 1, while motor 250 is active, threaded coupler 144 and connector 148 are rotated and reciprocated to effect rotation and reciprocation of inner cutting shaft 130. With respect to reciprocation in particular, inner cutting shaft 130, threaded coupler 144, and connector 148 are repeatedly reciprocated from respective proximal-most positions to respective distal-most positions and back to the respective proximal-most positions.

When connector 148 is displaced from the proximal-most position thereof, as illustrated in FIG. 4, proximally-facing surface 149b of connector 148 is spaced-apart from seal member 160 and, thus, proximally-facing cavity 149a of connector 148, which is disposed in fluid communication with the interior of inner cutting shaft 130, is also disposed in fluid communication with outflow conduit 220 of handpiece assembly 200 such that suction applied through outflow conduit 220 establishes vacuum within inner cutting shaft 130 to draw tissue through window 128 of elongated outer shaft 120 and into inner cutting shaft 130, while cutting edges 129, 138 facilitate cutting of tissue as it passes through window 128 and into inner cutting shaft 130. The cut tissue, fluids, and debris are suctioned through inner cutting shaft 130, proximally-facing cavity 149a of connector 148, outflow conduit 220 of handpiece assembly 200, and outflow tubing 400 to the collection reservoir.

However, when connector 148 is disposed in the proximal-most position thereof, as illustrated in FIG. 5, proximally-facing surface 149b of connector 148 is sealingly engaged with seal member 160, thus sealing proximally-facing cavity 149a of connector 148 from outflow conduit 220 of handpiece assembly 200 and inhibiting fluid communication therebetween. Thus, in the proximal-most position of connector 148, no suction is applied through inner cutting shaft 130.

The proximal-most position of connector 148 illustrated in FIG. 5 (which also corresponds to the proximal-most position of threaded coupler 144 and inner cutting shaft 130), wherein proximally-facing surface 149b of connector 148 is sealingly engaged with seal member 160, may correspond to an initial and/or home position of end effector assembly 100. More specifically, end effector assembly 100 may initially be disposed with connector 148 in its proximal-most position prior to engagement of end effector assembly 100 with handpiece assembly 200. Thus, upon engagement of end effector assembly 100 with handpiece assembly 200, proximally-facing cavity 149a of connector 148 is sealed off from outflow conduit 220 of handpiece assembly 200. Further, this initial position may be designated as a home position, whereby a control program (not shown) associated with motor 250 records the rotational position of drive rotor 260 upon engagement of end effector assembly 100 with handpiece assembly 200 (see FIG. 1) and, after activation, ensures that drive rotor 260 stops at a rotational position corresponding to the proximal-most position of connector 148 and, thus, a position where proximally-facing cavity 149a of connector 148 is sealed off from outflow conduit 220 of handpiece assembly 200.

The control program may utilize correlation information correlating, for example, rotation of drive rotor 260 with reciprocation of connector 148 to ensure that connector 148 is returned to its proximal-most position after each activation. As the correlating information may vary depending upon the particular end effector assembly 100 utilized, the control program may communicate with or read information from end effector assembly 100 in order to correlate rotation of drive rotor 260 with reciprocation of connector 148 and, thus, set the home position.

Figure 6:
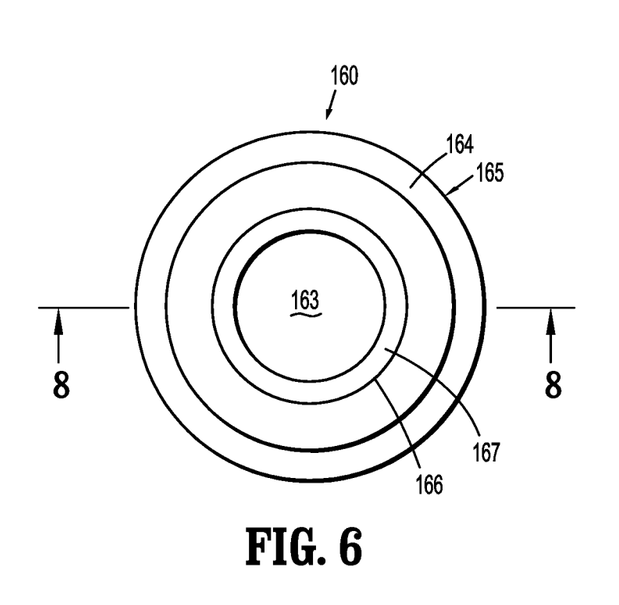
FIG. 6 is a front view of a seal member of the end effector assembly of FIG. 2.
Figure 7:
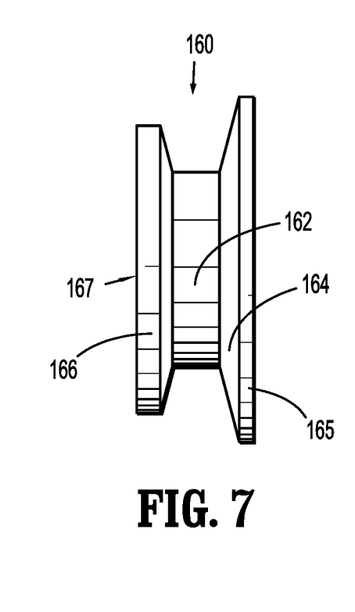
FIG. 7 is a side view of the seal member of FIG. 6.
Figure 8:
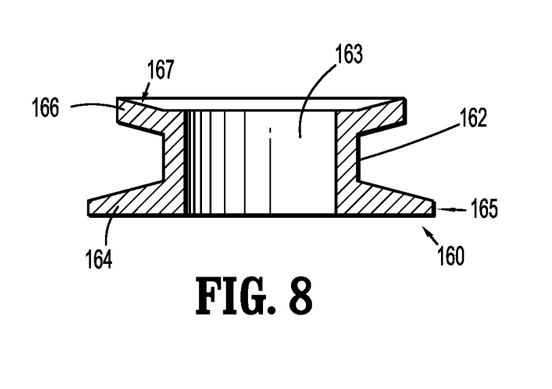
FIG. 8 is a longitudinal, cross-sectional view taken across section line "8-8" of FIG. 6.
Figure 9:
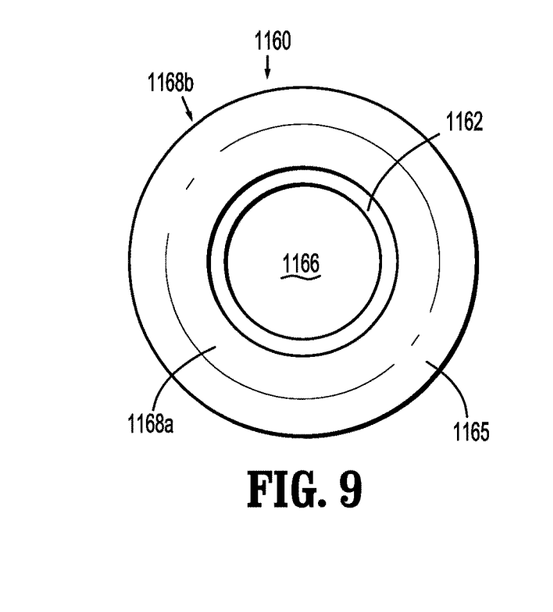
FIG. 9 is a front view of another seal member configured for use with the end effector assembly of FIG. 2.
Figure 10:
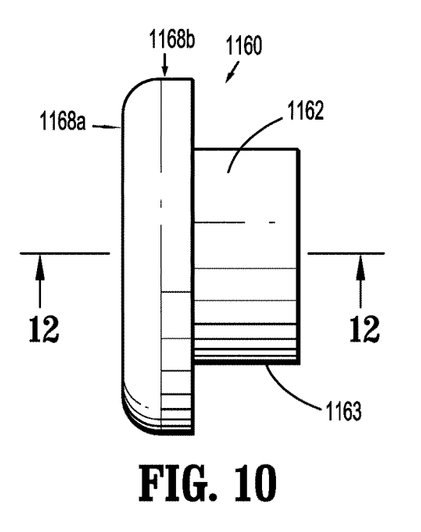
FIG. 10 is a side view of the seal member of FIG. 9.
Figure 11:
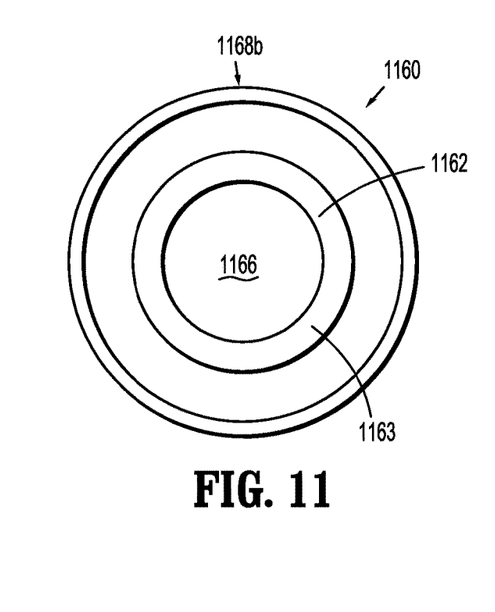
FIG. 11 is a rear view of the seal member of FIG. 9.
Figure 12:
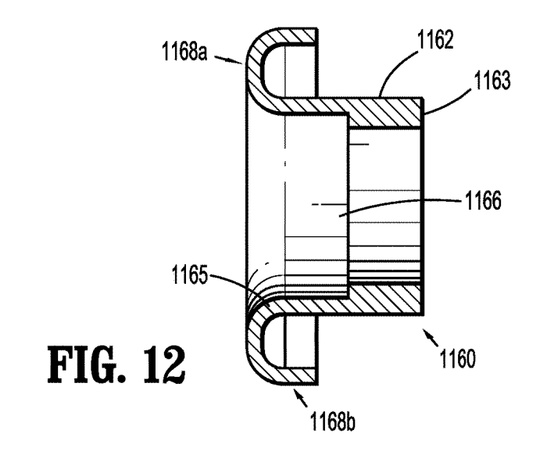
FIG. 12 is a longitudinal, cross-sectional view taken across section line "12-12" of FIG. 10.

Turning to FIGS. 6-8, seal member 160 is shown. Other suitable seal members configured for use with tissue resecting instrument 10 (FIG. 1) are also contemplated such as, for example, seal member 1160 (FIGS. 9-12). Seal member 160 includes a generally cylindrical body 162, a proximal rim 164 protruding radially outwardly from body 162, and a distal rim 166 protruding radially outwardly from body 162 at a position spaced-apart relative to proximal rim 164. Seal member 160 may be monolithically formed, e.g., molded, from any suitable material, e.g., silicone, rubber, PTFE, etc.

With additional reference to FIGS. 4 and 5, body 162 defined a longitudinal lumen 163 extending therethrough that is configured to receive distal spine 147c of proximal receiver 146 to secure seal member 160 about distal spine 147c. Distal rim 166 defines a distally-facing seal surface 167 and is configured to establish a seal against proximally-facing surface 149b of connector 148, in response to proximal-urging of proximally-facing surface 149b into contact with distally-facing seal surface 167, e.g., in the proximal-most position of connector 148 (see FIG. 5). In this manner, distal rim 166 functions as a face seal. An outer periphery 165 of proximal rim 164, on the other hand, is configured to sealingly engage an interior surface of proximal extension portion 114 of proximal hub housing 110 to inhibit any fluids disposed within proximal extension portion 114 of proximal hub housing 110 from passing proximally beyond seal member 160 and to inhibit fluid proximally of seal member 160 (but outside the outflow path) from being suctioned into the outflow path. Proximal rim 164 is configured as a dynamic seal in that outer periphery 165 thereof maintains a seal with the interior surface of proximal extension portion 114 of proximal hub housing 110 throughout rotation of distal spine 147c and, thus, seal member 160 relative to proximal extension portion 114 of proximal hub housing 110. Accordingly, seal member 160 provides a dual-seal configuration.

Turning to FIGS. 9-12, another seal member 1160 configured for use with tissue resecting instrument 10 (FIG. 1) is shown. Seal member 1160 includes a generally cylindrical body 1162 defining a proximal end portion 1163, a distal end portion 1165, and a lumen 1166 extending longitudinally therethrough. Distal end portion 1165 of seal member 1160 is inverted outwardly and back onto the exterior of body 1162 to define a distally-facing surface 1168a and a radially-outwardly-facing surface 1168b.

With additional reference to FIGS. 4 and 5, body 1162 is configured for positioning about distal spine 147c of proximal receiver 146 (with distal spine 147c extending through lumen 1166) to secure seal member 1160 about distal spine 147c. Distally-facing surface 1168a is configured to establish a seal against proximally-facing surface 149b of connector 148, in response to proximal-urging of proximally-facing surface 149b into contact with distally-facing seal surface 1168a, e.g., in the proximal-most position of connector 148 (see FIG. 5). In this manner, distally-facing surface 1168a functions as a face seal. Radially-outwardly-facing surface 1168b, on the other hand, is configured to sealingly engage an interior surface of proximal extension portion 114 of proximal hub housing 110 to inhibit any fluids disposed within proximal extension portion 114 of proximal hub housing 110 from passing proximally beyond seal member 1160 and to inhibit fluid proximally of seal member 1160 (but outside the outflow path) from being suctioned into the outflow path. Radially-outwardly-facing surface 1168b is configured as a dynamic seal that is configured to maintain a seal with the interior surface of proximal extension portion 114 of proximal hub housing 110 throughout rotation of distal spine 147c and, thus, seal member 1160 relative to proximal extension portion 114 of proximal hub housing 110. Accordingly, seal member 1160 provides a dual-seal configuration.

Referring generally to FIG. 1, as an alternative to handpiece assembly 200 configured for manual grasping and manipulation during use, tissue resecting instrument 10 may alternatively be configured for use with a robotic surgical system wherein handle housing 210 is configured to engage a robotic arm of the robotic surgical system. The robotic surgical system may employ various robotic elements to assist the surgeon and allow remote operation (or partial remote operation). More specifically, various robotic arms, gears, cams, pulleys, electric and mechanical motors, etc. may be employed for this purpose and may be designed with the robotic surgical system to assist the surgeon during the course of an operation or treatment. The robotic surgical system may include remotely steerable systems, automatically flexible surgical systems, remotely flexible surgical systems, remotely articulating surgical systems, wireless surgical systems, modular or selectively configurable remotely operated surgical systems, etc.

The robotic surgical system may be employed with one or more consoles that are next to the operating theater or located in a remote location. In this instance, one team of surgeons or nurses may prep the patient for surgery and configure the robotic surgical system with the surgical device disclosed herein while another surgeon (or group of surgeons) remotely control the surgical device via the robotic surgical system. As can be appreciated, a highly skilled surgeon may perform multiple operations in multiple locations without leaving his/her remote console which can be both economically advantageous and a benefit to the patient or a series of patients.

The robotic arms of the robotic surgical system are typically coupled to a pair of master handles by a controller. The handles can be moved by the surgeon to produce a corresponding movement of the working ends of any type of surgical instrument (e.g., end effectors, graspers, knifes, scissors, cameras, fluid delivery devices, etc.) which may complement the use of the tissue resecting devices described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. An end effector assembly of a tissue resecting instrument, the end effector assembly comprising:
    a proximal hub housing;
    an outer shaft extending from the proximal hub housing;
    an inner shaft disposed within the outer shaft and configured to rotate and reciprocate relative to the outer shaft for cutting tissue; and
    an inner core drive assembly disposed at least partially within the proximal hub housing, the inner core drive assembly operably coupled to the inner shaft and configured such that a rotational input provided to the inner core drive assembly effects the rotation and reciprocation of the inner shaft relative to the outer shaft, the inner core drive assembly including:
        a proximal receiver configured to receive the rotational input and to rotate relative to the proximal hub housing in response thereto, the proximal receiver including a seal member disposed thereon; and
        a connector operably coupled to the proximal receiver such that the rotation of the proximal receiver effects rotation of the connector relative to the proximal hub housing and reciprocation of the connector relative to the proximal receiver and the proximal hub housing between a proximal position and a distal position, the connector operably coupled to the inner shaft such that the rotation and reciprocation of the connector effects the rotation and reciprocation of the inner shaft, the connector defining a cavity disposed in fluid communication with an interior of the inner shaft, wherein, in the proximal position, the connector abuts the seal member to establish a seal that blocks outflow from the cavity, and wherein, in the distal position, the connector is displaced from the seal member to permit outflow from the cavity.

2. The end effector assembly according to claim 1, wherein the inner core drive assembly further includes:
    a threaded coupler operably coupled to the connector; and
    a follower operably engaged with the threaded coupler, wherein the rotation of the connector in response to the rotation of the proximal receiver rotates the threaded coupler relative to the follower, thereby reciprocating the threaded coupler and the connector relative to the proximal receiver.

3. The end effector assembly according to claim 1, wherein the connector is rotationally fixed relative to the proximal receiver via at least partial receipt of a distal spine of the proximal receiver within the cavity of the connector.

4. The end effector assembly according to claim 3, wherein the distal spine is slidable relative to the cavity of the connector to permit the reciprocation of the connector relative to the proximal receiver.

5. The end effector assembly according to claim 3, wherein the seal member is disposed about the distal spine.

6. The end effector assembly according to claim 1, wherein the reciprocation of the connector effects similar reciprocation of the inner shaft.

7. The end effector assembly according to claim 1, wherein gearing is operably coupled between the connector and the inner shaft such that the rotation of the inner shaft is amplified or attenuated relative to the rotation of the connector.

8. The end effector assembly according to claim 1, wherein the outer shaft defines a window, and wherein the inner shaft is configured to rotate and reciprocate relative to the window to cut tissue extending through the window.

9. The end effector assembly according to claim 1, wherein the proximal position of the connector corresponds to a proximal position of the inner shaft relative to the outer shaft.

10. A tissue resecting instrument, comprising:
    a handpiece assembly including a drive rotor and an outflow conduit; and
    an end effector assembly configured to releasably engage the handpiece assembly, the end effector assembly comprising:
        an outer shaft;
        an inner shaft disposed within the outer shaft and configured to rotate and reciprocate relative to the outer shaft for cutting tissue; and
        an inner core drive assembly, including:
            a proximal receiver configured to receive a rotational input from the drive rotor and to rotate in response thereto, the proximal receiver including a seal member disposed thereon; and
            a connector operably coupled to the proximal receiver such that the rotation of the proximal receiver effects rotation of the connector and reciprocation of the connector between a proximal position and a distal position, the connector operably coupled to the inner shaft such that the rotation and reciprocation of the connector effects the rotation and reciprocation of the inner shaft, the connector defining a cavity disposed in fluid communication with an interior of the inner shaft, wherein, in the proximal position, the connector abuts the seal member to establish a seal that blocks outflow from the cavity into the outflow conduit, and wherein, in the distal position, the connector is displaced from the seal member to permit outflow from the cavity into the outflow conduit.

11. The tissue resecting instrument according to claim 10, wherein the handpiece assembly further includes a motor configured to drive rotation of the drive rotor.

12. The tissue resecting instrument according to claim 10, wherein the inner core drive assembly further includes:
    a threaded coupler operably coupled to the connector; and
    a follower operably engaged with the threaded coupler, wherein the rotation of the connector in response to the rotation of the proximal receiver rotates the threaded coupler relative to the follower, thereby reciprocating the threaded coupler and the connector relative to the proximal receiver.

13. The tissue resecting instrument according to claim 10, wherein the connector is rotationally fixed relative to the proximal receiver via at least partial receipt of a distal spine of the proximal receiver within the cavity of the connector.

14. The tissue resecting instrument according to claim 13, wherein the distal spine is slidable relative to the cavity of the connector to permit the reciprocation of the connector relative to the proximal receiver.

15. The tissue resecting instrument according to claim 13, wherein the seal member is disposed about the distal spine.

16. The tissue resecting instrument according to claim 10, wherein the reciprocation of the connector effects similar reciprocation of the inner shaft.

17. The tissue resecting instrument according to claim 10, wherein gearing is operably coupled between the connector and the inner shaft such that the rotation of the inner shaft is amplified or attenuated relative to the rotation of the connector.

18. The tissue resecting instrument according to claim 10, wherein the outer shaft defines a window, and wherein the inner shaft is configured to rotate and reciprocate relative to the window to cut tissue extending through the window.

19. The tissue resecting instrument according to claim 10, wherein the proximal position of the connector corresponds to a proximal position of the inner shaft relative to the outer shaft.

20. The tissue resecting instrument according to claim 10, wherein the drive rotor is configured to provide a further rotational input to the proximal receiver after the rotational input to the proximal receiver to return the connector to the proximal position, thereby establishing the seal that blocks outflow from the cavity into the outflow conduit.

* * * * *